(12) United States Patent
Livorsi et al.

(10) Patent No.: US 9,314,254 B2
(45) Date of Patent: Apr. 19, 2016

(54) METHODS AND DEVICES FOR REMOVING A SPINAL DISC

(71) Applicant: DePuy Synthes Products, Inc., Raynham, MA (US)

(72) Inventors: Carl Livorsi, Lakeville, MA (US); Francisco A. Amaral, Acushnet, MA (US); Paul Monteiro, Somerset, MA (US); Rod G. Cameron, Franklin, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 252 days.

(21) Appl. No.: 13/836,265

(22) Filed: Mar. 15, 2013

(65) Prior Publication Data
US 2014/0276834 A1    Sep. 18, 2014

(51) Int. Cl.
*A61B 17/16*   (2006.01)
*A61B 17/00*   (2006.01)
*A61B 17/32*   (2006.01)

(52) U.S. Cl.
CPC ... *A61B 17/1671* (2013.01); *A61B 2017/00261* (2013.01); *A61B 2017/320064* (2013.01)

(58) Field of Classification Search
CPC .............. A61B 17/16; A61B 17/1604; A61B 17/1606; A61B 17/1608; A61B 17/1611; A61B 17/1635; A61B 17/1642; A61B 17/1662; A61B 17/1671; A61B 2017/00261; A61B 2017/320064; B25D 3/00
USPC ................. 606/184, 205–206; 30/167–167.2
See application file for complete search history.

(56) References Cited

U.S. PATENT DOCUMENTS

| | | | | | |
|---|---|---|---|---|---|
| 3,628,522 | A | * | 12/1971 | Kato | ............................ 600/564 |
| 4,777,948 | A | * | 10/1988 | Wright | ............................ 606/83 |
| 4,881,550 | A | | 11/1989 | Kothe | |

(Continued)

FOREIGN PATENT DOCUMENTS

| | | |
|---|---|---|
| GB | 2 469 082 A | 10/2010 |
| WO | 93/19675 A1 | 10/1993 |
| WO | 2010/013188 A1 | 2/2010 |

OTHER PUBLICATIONS

International Search Report and Written Opinion for Application No. PCT/US2014/018992, mailed Jun. 5, 2014 (13 pages).

(Continued)

*Primary Examiner* — Christian Sevilla
*Assistant Examiner* — Eric S Gibson
(74) *Attorney, Agent, or Firm* — Nutter McClennen & Fish LLP

(57) ABSTRACT

Devices and methods for removing a spinal disc are provided herein. Discectomy instruments are disclosed that can remove a spinal disc in a single-pass, i.e., without repeatedly inserting and removing the instrument from a patient. In an exemplary embodiment, the discectomy instrument includes a distal housing, at least one cutting blade, and a handle. When the distal housing is positioned adjacent to a spinal disc, a handle can be actuated to advance the cutting blade along a substantially arc-shaped path through the disc. In certain aspects, the path of the blade can correspond to the anatomy of the disc and to the approach used to access the spine. A second cutting blade can be advanced through the disc and can intersect with the arc-shaped path, forming a complete cut. The cut disc can be received in the distal housing and removed from the patient.

14 Claims, 20 Drawing Sheets

(56) References Cited

U.S. PATENT DOCUMENTS

| | | | |
|---|---|---|---|
| 4,941,466 A * | 7/1990 | Romano | 606/80 |
| 5,002,546 A * | 3/1991 | Romano | 606/80 |
| 5,061,269 A * | 10/1991 | Muller | 606/83 |
| 5,366,476 A * | 11/1994 | Noda | 606/206 |
| 5,456,684 A * | 10/1995 | Schmidt et al. | 606/41 |
| 5,476,473 A * | 12/1995 | Heckele | 606/171 |
| 5,509,918 A * | 4/1996 | Romano | 606/80 |
| 5,562,736 A * | 10/1996 | Ray et al. | 606/86 A |
| 5,620,458 A * | 4/1997 | Green et al. | 606/188 |
| 5,649,945 A * | 7/1997 | Ray et al. | 606/167 |
| 5,676,636 A * | 10/1997 | Chin | 600/209 |
| 5,827,323 A * | 10/1998 | Klieman et al. | 606/205 |
| 5,830,215 A * | 11/1998 | Incavo et al. | 606/79 |
| 5,925,050 A * | 7/1999 | Howard, III | 606/83 |
| 5,984,939 A * | 11/1999 | Yoon | 606/170 |
| 6,174,311 B1 * | 1/2001 | Branch et al. | 606/86 A |
| 6,214,010 B1 * | 4/2001 | Farley et al. | 606/83 |
| 6,299,625 B1 * | 10/2001 | Bacher | 606/170 |
| 6,383,191 B1 * | 5/2002 | Zdeblick et al. | 606/105 |
| 6,391,043 B1 * | 5/2002 | Moll et al. | 606/174 |
| 6,409,678 B1 * | 6/2002 | Ouchi | 600/562 |
| 6,500,189 B1 * | 12/2002 | Lang et al. | 606/170 |
| 6,575,899 B1 * | 6/2003 | Foley et al. | 600/114 |
| 6,773,444 B2 * | 8/2004 | Messerly | 606/169 |
| 7,410,494 B2 * | 8/2008 | Kalmann et al. | 606/205 |
| 8,573,090 B2 * | 11/2013 | Isobe et al. | 74/490.04 |
| 2001/0037128 A1 * | 11/2001 | Arambula | 606/198 |
| 2001/0044635 A1 * | 11/2001 | Niizeki et al. | 606/205 |
| 2002/0022856 A1 * | 2/2002 | Johnson et al. | 606/185 |
| 2002/0165580 A1 * | 11/2002 | Zwiefel et al. | 606/205 |
| 2003/0028197 A1 * | 2/2003 | Hanson et al. | 606/99 |
| 2003/0065358 A1 * | 4/2003 | Frecker et al. | 606/205 |
| 2003/0083664 A1 * | 5/2003 | Rogers et al. | 606/79 |
| 2003/0199874 A1 * | 10/2003 | Michelson | 606/61 |
| 2004/0267164 A1 * | 12/2004 | Rhodes et al. | 600/587 |
| 2004/0267304 A1 * | 12/2004 | Zannis et al. | 606/206 |
| 2005/0080422 A1 * | 4/2005 | Otte et al. | 606/85 |
| 2005/0090829 A1 * | 4/2005 | Martz et al. | 606/79 |
| 2005/0113838 A1 * | 5/2005 | Phillips et al. | 606/80 |
| 2005/0137453 A1 * | 6/2005 | Ouchi et al. | 600/106 |
| 2005/0251146 A1 * | 11/2005 | Martz et al. | 606/84 |
| 2006/0116689 A1 * | 6/2006 | Albans et al. | 606/92 |
| 2006/0241566 A1 * | 10/2006 | Moon et al. | 604/540 |
| 2006/0258954 A1 * | 11/2006 | Timberlake et al. | 600/564 |
| 2007/0073185 A1 * | 3/2007 | Nakao | 600/564 |
| 2007/0106297 A1 * | 5/2007 | Dumbauld et al. | 606/51 |
| 2007/0123890 A1 * | 5/2007 | Way et al. | 606/79 |
| 2007/0162061 A1 * | 7/2007 | Way et al. | 606/167 |
| 2007/0173814 A1 * | 7/2007 | Hixson et al. | 606/51 |
| 2007/0255278 A1 * | 11/2007 | Nobis et al. | 606/45 |
| 2008/0058674 A1 | 3/2008 | Jansen et al. | |
| 2008/0086133 A1 * | 4/2008 | Kuslich et al. | 606/61 |
| 2009/0062805 A1 * | 3/2009 | Casutt | 606/83 |
| 2009/0204119 A1 * | 8/2009 | Bleich et al. | 606/79 |
| 2009/0209991 A1 * | 8/2009 | Hinchliffe et al. | 606/170 |
| 2010/0121153 A1 * | 5/2010 | To | 600/214 |
| 2010/0179578 A1 * | 7/2010 | Tannoury et al. | 606/170 |
| 2010/0206099 A1 * | 8/2010 | Diao et al. | 73/866.5 |
| 2011/0040301 A1 * | 2/2011 | Blain et al. | 606/80 |
| 2011/0098531 A1 * | 4/2011 | To | 600/114 |
| 2011/0118789 A1 * | 5/2011 | Siegal | 606/279 |
| 2011/0124961 A1 * | 5/2011 | Zimmon | 600/104 |
| 2011/0276085 A1 * | 11/2011 | Krzyzanowski | 606/208 |
| 2012/0065466 A1 * | 3/2012 | Slater | 600/104 |
| 2012/0065659 A1 * | 3/2012 | To | 606/192 |
| 2012/0239072 A1 * | 9/2012 | Rodriguez | 606/185 |
| 2013/0018376 A1 * | 1/2013 | Yoon et al. | 606/79 |
| 2013/0018377 A1 * | 1/2013 | Williams | 606/85 |
| 2013/0123797 A1 * | 5/2013 | Livneh | 606/114 |
| 2013/0237843 A1 * | 9/2013 | Linares et al. | 600/476 |
| 2013/0289399 A1 * | 10/2013 | Choi et al. | 600/431 |
| 2014/0155901 A1 * | 6/2014 | Jacobs | 606/82 |
| 2014/0180414 A1 * | 6/2014 | Pfeiffer et al. | 623/16.11 |
| 2014/0276834 A1 * | 9/2014 | Livorsi et al. | 606/79 |
| 2014/0303625 A1 * | 10/2014 | Sholev et al. | 606/80 |
| 2014/0316209 A1 * | 10/2014 | Overes et al. | 600/206 |
| 2015/0038973 A1 * | 2/2015 | Grim | 606/83 |
| 2015/0045795 A1 * | 2/2015 | Sholev et al. | 606/79 |

OTHER PUBLICATIONS

International Preliminary Report on Patentability for Application No. PCT/US2014/018992, mailed Sep. 24, 2015 (9 pages).

* cited by examiner

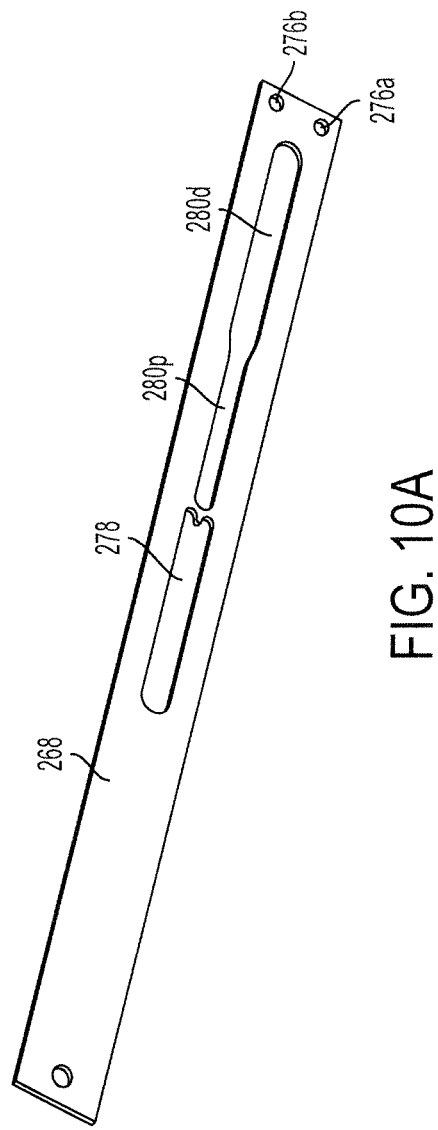

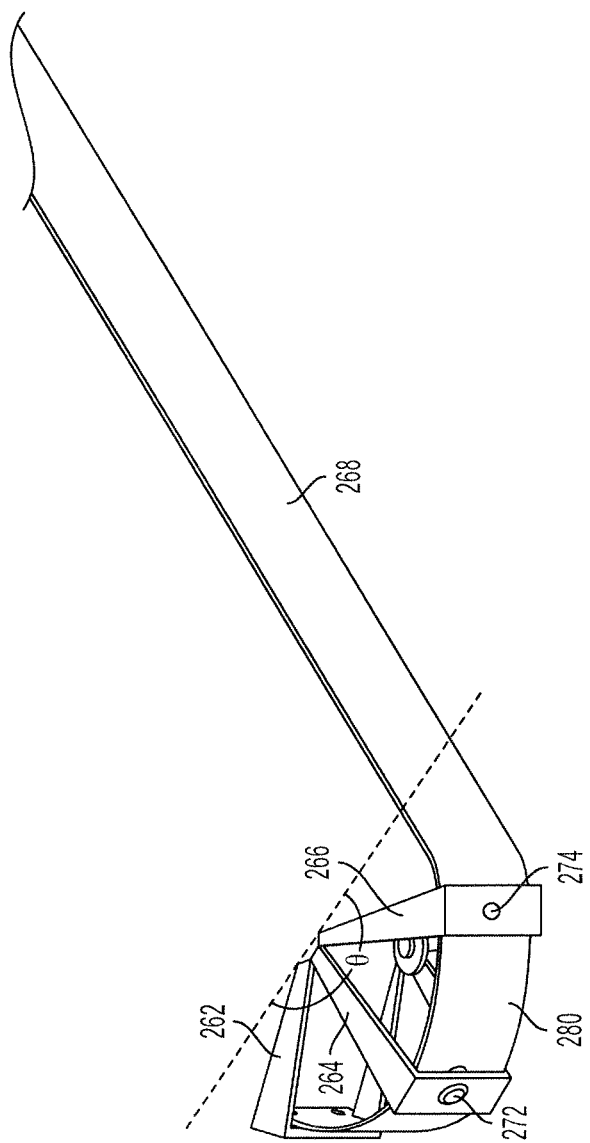

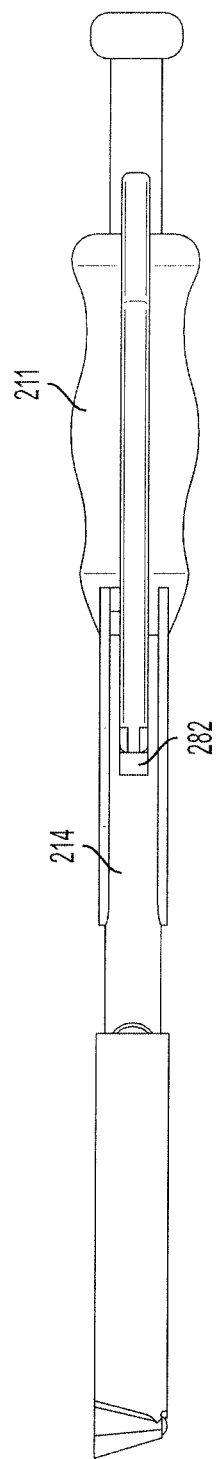

METHODS AND DEVICES FOR REMOVING A SPINAL DISC

FIELD

The present invention relates generally to methods and devices for removing a spinal disc.

BACKGROUND

Spinal fusion surgeries, that is, the use of bone graft material to promote specific vertebrae to grow together into a solid and stable construct, are a common method of treating patients with severe back pain. For fusion to occur within the disc space, the surgeon must first remove the damaged disc material. During and/or or subsequent to the removal of the disc material, the empty space left between the upper and lower vertebrae can be distracted to relieve pressure from neural elements and to provide space for entry of surgical tools and/or implants. A bone graft, or interbody cage with bone, is then inserted into the empty disc space to promote bone growth from vertebral body to vertebral body. Recently, minimally invasive techniques have improved fusion procedures by causing less damage to tissue surrounding the damaged disc and allowing for faster recovery by the patient.

The initial step of removing the disc material from the intervertebral space is important because it facilitates fusion of the vertebrae. However, there are drawbacks with prior art instruments and techniques for removing a spinal disc. In a typical minimally invasive spinal fusion procedure, a small access port is formed in a patient that provides access to the disc. An instrument, such as a pituitary rongeur, is inserted through the access port and positioned between the vertebrae. The jaws of the pituitary rongeur are closed to engage a small piece of disc. The surgeon removes the instrument from the patient and scrapes off the small piece of disc material from the jaws. This process is repeated numerous times until the nucleus fibrosis and annulus of the disc are partly or completely removed. Because conventional instruments can only receive small pieces of disc material at a time, it can take up to 30 minutes for a surgeon to thoroughly remove the disc material. The small size of the access port can also make it difficult for a surgeon to manipulate an instrument and reach particular areas of the disc. Further, repeatedly inserting and removing sharp instruments from a patient can cause damage to soft tissue and nerves.

Accordingly, there remains a need for improved surgical instruments and methods for removing a spinal disc.

SUMMARY OF THE INVENTION

Devices for removing a spinal disc from a patient are provided herein. In one embodiment, a device for removing a spinal disc includes a housing, a first blade actuator, and a second blade actuator. The housing can have four walls that form a substantially rectangular shape with an open interior configured to receive a cut portion of a spinal disc. The first blade actuator can have a distal end that is operatively coupled to a first cutting blade, and the second blade actuator can have a distal end operatively coupled to a second cutting blade. The first blade actuator can be configured to move the first cutting blade along an arc-shaped path through a spinal disc, and the second actuator element can be configured to move the second cutting blade such that the second cutting blade contacts the first cutting blade, thereby cutting the spinal disc.

The device can have features that relate to a size of the spinal disc. For example, the arc-shaped path of the first cutting blade can substantially correspond to a shape of a lateral surface of the spinal disc. As another example, the housing can have a height that is greater than or substantially equal to a height of the spinal disc.

The device can vary in other ways. In one embodiment, the first cutting blade includes a swing blade having at least one cutting edge. The cutting edge of the swing blade can be configured to pivot to an angle of about 165 degrees relative to a distal end of the housing. The device can further include a timing band configured to slide relative to the housing to advance the swing blade along the arc-shaped path in response to movement of the first blade actuator. In certain aspects, the device can further include at least one swing blade stabilizer configured to selectively mate with the timing band when the timing band moves relative to the housing.

In another embodiment, the first cutting blade and the second cutting blade are configured to move within one or more guide features formed in the housing. In certain aspects, distal ends of the first and second cutting blades are configured to interlock.

Methods for removing a spinal disc from an intervertebral space are also provided herein. This can include positioning a distal portion of an instrument adjacent to an intervertebral space, the instrument having first and second cutting blades. The method can further include advancing the first cutting blade along a substantially circular path to form a cut in the spinal disc, and advancing the second cutting blade through the spinal disc until a distal end of the second cutting blade contacts the first cutting blade. The instrument can be retracted to remove the spinal disc from the intervertebral space.

The method can vary in any number of ways. In one embodiment, the method can further include accessing the intervertebral space via a lateral approach. In another embodiment, the method can further include accessing the intervertebral space via a posterior approach. In yet another embodiment, the intervertebral space can be distracted prior to advancing the first cutting blade along the substantially circular path.

A size or volume of the spinal disc cut from the intervertebral space can vary. In certain aspects, the second cutting blade contacts the first cutting blade and cuts at least a portion of the spinal disc. For example, advancing the first cutting blade and advancing the second cutting blade can cut at least 25% of the spinal disc by volume. As another example, advancing the first cutting blade and advancing the second cutting blade cuts at least 50% of the spinal disc by volume.

The first cutting blade and the second cutting blade can be moved in different ways. In one embodiment, the first cutting blade and the second cutting blade are advanced at an angle of about 90 degrees relative to an axis. In another embodiment, the first cutting blade is a swing blade, and advancing the swing blade includes pivoting the swing blade to an angle of at least 90 degrees relative to an axis. In certain aspects, advancing the second cutting blade includes moving the second cutting blade distally until the distal end of the second cutting blade contacts a distal end of the first cutting blade.

After retracting the instrument and removing the spinal disc, a spinal fusion cage can be inserted into the intervertebral space.

BRIEF DESCRIPTION OF THE DRAWINGS

The present invention will be more fully understood from the following detailed description taken in conjunction with the accompanying drawings, in which:

FIG. 10A is a perspective view of a timing band;

FIG. 10B is a perspective view of the timing band and swing blade assembly of the instrument of FIG. 8 in a deployed configuration;

FIG. 11B is a side view of the instrument of FIG. 11A;

DETAILED DESCRIPTION

Figure 1:
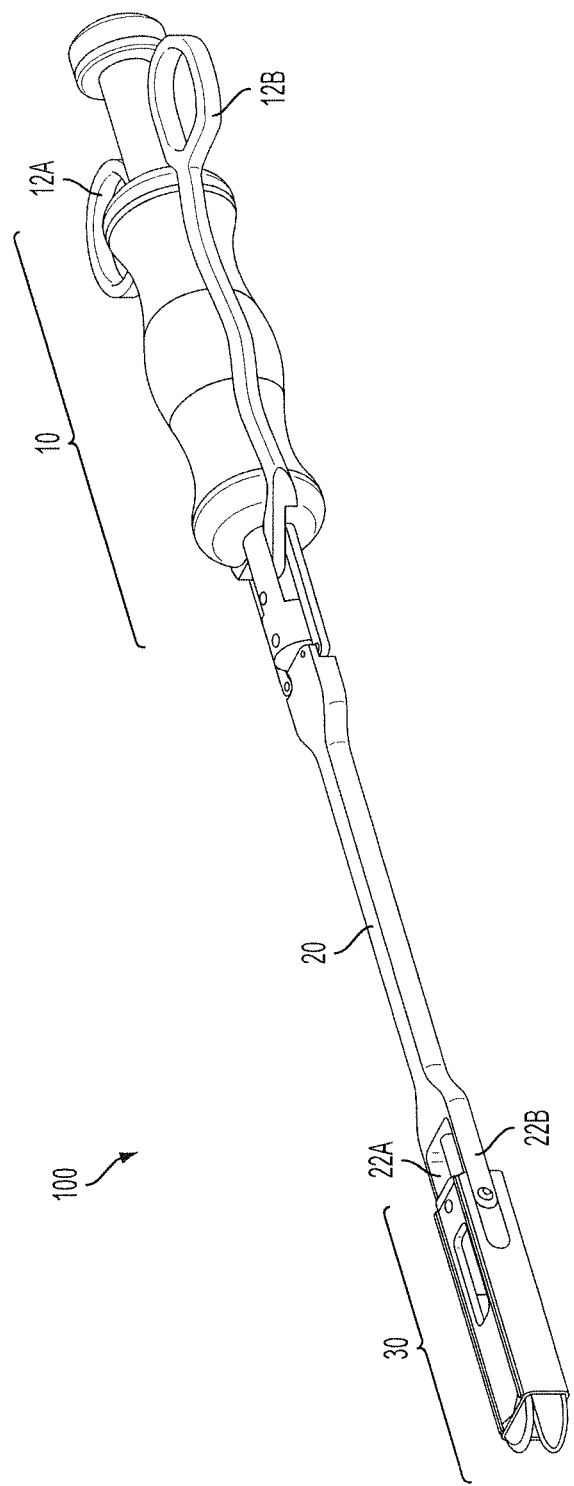
FIG. 1 is a perspective view of a first embodiment of a discectomy instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. As used herein, the term "proximal" refers to a direction closest to a user and "distal" refers to a direction closest to a surgical site.

Devices and methods for removing a spinal disc are provided herein. In general, discectomy instruments are disclosed that can be used to remove a spinal disc in a single-pass, i.e., without repeatedly inserting and removing the instrument from a patient. In an exemplary embodiment, a discectomy instrument can include a distal housing, at least one cutting blade, and a handle. When the distal housing is positioned adjacent to or within a spinal disc, a handle on the proximal end of the instrument can be actuated to advance the cutting blade along a substantially arc-shaped path through the disc. The path of the cutting blade can correspond to the anatomy of the disc and to the particular approach used to access the spine (e.g. lateral, posterior, anterior). A second cutting blade can be advanced through the disc and intersect with the arc-shaped path, thereby forming a complete cut. In some embodiments, the actuator can be manually operated and can provide tactile feedback to the user. After the disc is cut, it can be received in the distal housing, and the instrument and the cut disc can be removed from the patient. As will be appreciated by persons skilled in the art, the devices and methods disclosed herein can be used during both open and minimally invasive surgery (MIS).

FIG. 1 illustrates one exemplary embodiment of a discectomy instrument 100 that includes a handle assembly 10, a shaft body 20, and a distal housing 30 configured to cut through a spinal disc. In the illustrated embodiment, the handle assembly 10 includes first and second blade actuators 12A, 12B that are movable toward and away from a central handle 14 to actuate cutting blades (not shown) disposed in the distal housing 30. The shaft body 20 can be coupled to the handle assembly 10 and can have a generally elongate shape terminating in first and second arms 22A, 22B. The distal housing 30 can reside in between and extend from the first and second arms 22A, 22B. The distal housing 30 can have an elongate rectangular shape and can the one or more cutting blades that are movable relative to the housing 30. As will be discussed, the discectomy instrument 100 can be used to remove a spinal disc, and is particularly suited to remove a disc accessed via a lateral approach.

Figure 2:
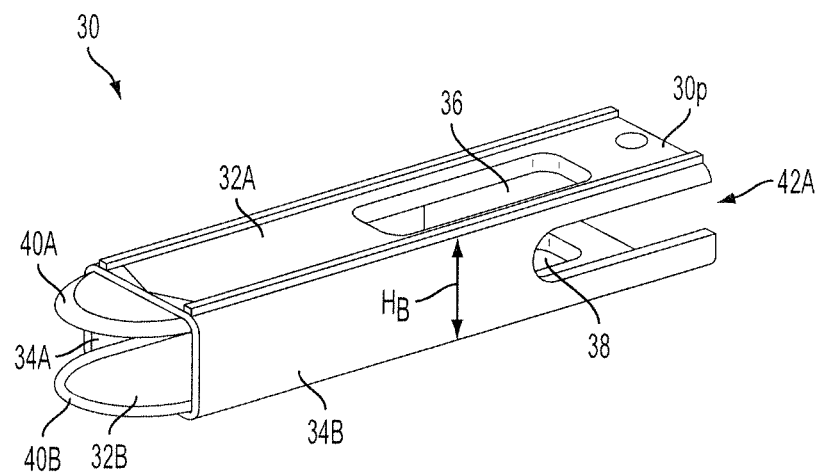
FIG. 2 is a perspective view of a distal housing of FIG. 1.

The distal housing can have various sizes, shapes, and configurations. In general, the distal housing can house one or more cutting blades and can have an open interior configured to receive a cut portion of a spinal disc. In the embodiment of FIG. 2, the distal housing 30 has an elongate rectangular shape defined by four walls, referred to herein as top and bottom walls 32A, 32B and first lateral and second lateral walls 34A, 34B, that form an elongate, generally rectangular shape. In use, the top wall 32A can be configured to contact a first vertebral endplate and the bottom wall 32B can be configured to contact a second vertebral endplate. The top and bottom walls 32A, 32B of the distal housing 30 can have various features and configurations. For example, the top wall 32A can have an elongate, rectangular slot 36 formed therein for extracting a cut portion of a spinal disc therethrough. The bottom wall 32B can have the same general size and shape as the top wall 32A, and can be substantially opposed to the top wall 32A. The bottom wall 32B can further include an elongate, rectangular slot 38 formed therein for extracting a cut portion of a spinal disc therethrough. In the illustrated embodiment, top and bottom walls 32A, 32B have a substantially rectangular shape with a distal edge 40A, 40B that can extend beyond distal ends of each of the lateral walls 34A, 34B and can thus be configured to cut through a spinal disc when the distal housing 30 is inserted therein. As will be explained in greater detail below, a geometry of the distal edges 40A, 40B can be selected to match a spinal fusion cage to be inserted into the intervertebral disc space following removal of the cut portion of the disc. As shown in FIG. 2, the distal edges 40A, 40B are arc-shaped or curved, but other configurations are possible. In certain aspects, the distal edges 40A, 40B can be sharpened and/or serrated so that the instrument is configured to cut through a spinal disc.

The first and second lateral walls 34A, 34B of the distal housing 30 can also have various sizes, shapes, and configurations. The first lateral wall 34A can have the same size and shape as the second lateral wall 34B and can be substantially opposed to the second lateral wall 34B, thereby forming the rectangular shape of the distal housing 30. Each of the lateral walls 34A, 34B can also include a feature for coupling to the shaft body. The lateral walls 34A, 34B can have an elongate, generally rectangular shaped cutout formed therein and referred to herein as a recess 42A, 42B, for receiving the first and second arms 22A, 22B of the shaft body 20. FIG. 2 shows the recess 42B of the second lateral wall 34B. More specifically, the recesses 42A, 42B can extend from a proximal end 30p of the housing 30 distally along approximately 25-50% of a longitudinal length of the lateral walls 34A, 34B. Heights $H_A$ and $H_B$ (not shown) of each of the first and second lateral walls 34A, 34B can vary according to a desired use. For example, a height of each of the lateral walls 34A, 34B can substantially correspond to a height of a spinal disc disposed between adjacent vertebrae. In other aspects, the height of the lateral walls 34A, 34B can be selected such that the distal housing 30 is configured to distract or push apart adjacent vertebrae to provide space for a fusion cage to be inserted therein and/or to help decompress a collapsed spinal disc.

Figure 3A:
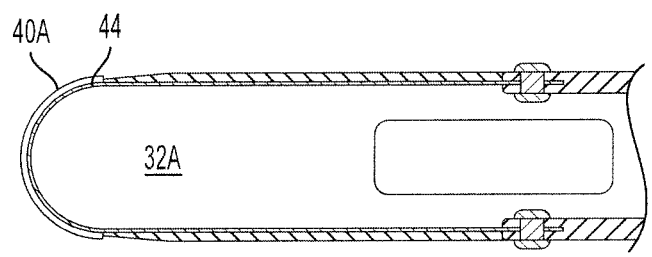
FIG. 3A is a side view of a first inner face of the distal housing.
Figure 3B:
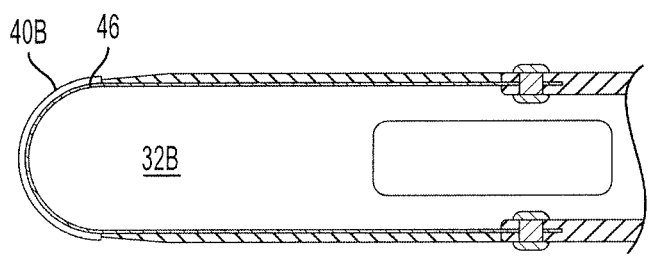
FIG. 3B is a side view of a second inner face of the distal housing.

The distal housing can have at least one guide feature configured to receive a cutting blade therein. As shown in FIGS. 3A and 3B, the distal housing 30 has two guide features consisting of a first track 44 formed on an inner face of the top wall 32A and a second track 46 formed on an inner face of the bottom wall 32B. First and second blades (not shown) can slide within the first and second tracks 44, 46, respectively, as will be discussed in greater detail below. As shown, the first and second tracks 44, 46 can be formed along an outer edge of the inner faces so that the path of each cutting blade substantially corresponds to or mimics the curved shape of the distal edge 40A, 40B. While the illustrated embodiment has two guide features or tracks, the distal housing can have any number guide features with various configurations. By way of non-limiting example, in another embodiment a single track can be formed on an inner face of the top or bottom wall of the distal housing.

Figure 4:
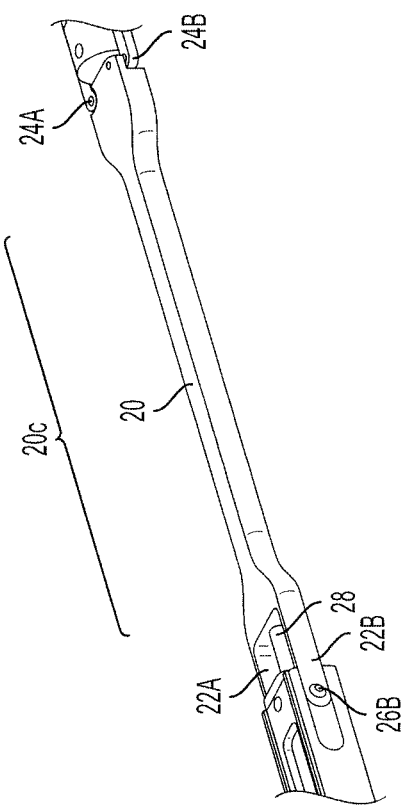
FIG. 4 is a perspective view of a shaft body of the instrument of FIG. 1.

The shaft body can be a backbone of the instrument and can be disposed between the distal housing and the handle assembly. As shown in FIG. 4, the shaft body 20 can have a generally elongate shape and proximal and distal ends 20p, 20d. The proximal end 20p of the shaft body 20 can be configured to mate with the first and second blade actuators 12A, 12B, while the distal end 20d of the shaft body 20 can mate with the distal housing 30. In particular, the proximal end 20p of the shaft body 20 can have first and second bores 24A, 24B formed therein configured to couple to two linkage bars, as will be discussed below. The distal end 20d of the shaft body 20 can terminate in first and second parallel arms 22A, 22B that extend in a proximal-to-distal direction, parallel to a longitudinal axis of the shaft body 20. In the illustrated embodiment, the first and second arms 22A, 22B have a rounded/curved distal tip 26A, 26B that can slide into a cutout formed in each of the first and second lateral walls 34A, 34B of the distal housing 30, as will be explained in greater detail below. The shaft body can further include an inner lumen (not shown) for receiving an inner shaft 28 therein. As will be appreciated by a person skilled in the art, the shaft body 20 can have various sizes and configurations. In the illustrated embodiment, the shaft body has four sides, the top and bottom sides being substantially planar and the lateral sides being curved. Additionally, a central portion 20c of the shaft body 20 can taper in and thus have a smaller width than a width of the proximal and distal ends of the shaft body. Because the first and second arms 22A, 22B of the shaft body 22 receive the distal housing 30 therein, a distance between the arms can be substantially equal to a width of the distal housing. The width of the distal housing can be defined by a width of the top and bottom sides 32A, 32B.

Figure 5:
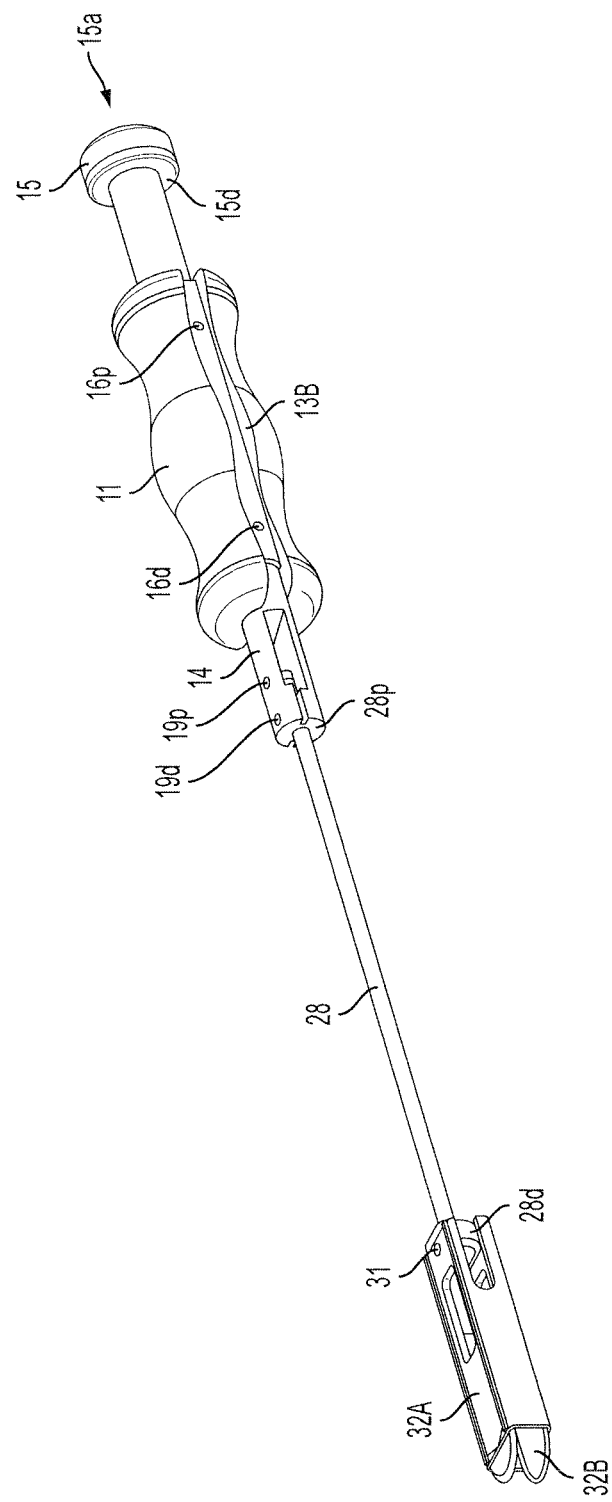
FIG. 5 is a perspective view of components of the distal housing and handle assembly that are stationary relative to one another and are coupled together via an inner shaft.

The inner shaft can be disposed in the inner lumen of the shaft body and can have various sizes, shapes, and configurations. As shown in FIG. 5, the inner shaft 28 can have a generally elongate shape with proximal and distal ends 28p, 28d. The inner shaft 28 can be coupled to a proximal end 30p of the distal housing 30 and a distal end of a shaft 14 of the handle assembly 10. More specifically, the proximal end 28p of the inner shaft 28 can be coupled to the shaft 14 of the handle assembly 10 by one or more pins as mentioned above, while the distal end 28d of the inner shaft 28 can be coupled to the distal housing 30 by a pin 31. The inner shaft 28 can be coupled to the distal housing 30 and to the shaft 14 of the handle assembly 10 in other ways including, by way of non-limiting example, spot-weld, etc. In one embodiment, a diameter of the inner shaft 28 can vary along the proximal-to-distal length. For example, a portion of the inner shaft 28 that extends through the inner lumen of the shaft body 20 can have a first diameter, while the distal end 28d of the inner shaft 28 that resides in the distal housing 30 can have a second diameter. In certain aspects, the distal end 28d of the inner shaft 28 can have a diameter that is substantially equal to a width of the top and bottom walls 32A, 32B of the housing 30, and this can provide rigidity to the distal housing 30.

The handle assembly can be manipulated by a user and can have various features and configurations. The handle assembly 10 can include a grasping handle 11, as shown in FIG. 4. In certain aspects, the grasping handle 11 can have an elongate, generally cylindrical shape with a contoured outer surface that facilitates being grasped by a user. The handle assembly can also include the shaft 14 previously mentioned, and a proximal end 14p of the shaft 14 can terminate in a striking head 15 having a cylindrical shape and a flattened, substantially planar proximal surface 15p. In one embodiment, the grasping handle 11 can be disposed around and can be slidable relative to the shaft 14. As will be discussed below, a hammer can be used to strike the proximal surface 15p of the head 15 to drive the instrument through a body. In certain aspects, after the device is actuated to cut a portion of a spinal disc, a user can slide the grasping handle 11 proximally relative to the shaft 14 until it contacts a distal surface 15d of the striking head 15, thereby exerting a proximally directed force on the instrument to withdraw it from a patient. The handle assembly can have other configurations. For example, in another embodiment, the grasping handle can be stationary relative to the shaft of the handle assembly, and integrally formed with or molded to the shaft.

The grasping handle can further include one or more depressions, referred to herein as longitudinal recesses, configured to receive cutting blade actuators therein. In the illustrated embodiment, the grasping handle 11 has first and second longitudinal recesses 13A, 13B that extend in a proximal to distal direction relative to a longitudinal axis of the grasping handle 11. These recesses 13A, 13B can also have one or more mating features configured to hold the knife blade actuators 12A, 12B substantially flush against the grasping handle 11. In the illustrated embodiment, the mating features are circular indentations 16p, 16d that can receive corresponding circular protrusions (not shown) formed on each of the blade actuators 12A, 12B. The grasping handle can have other features and configurations that allow it to mate with the blade actuators.

The shaft of the handle assembly can have additional features. In the illustrated embodiment, the shaft 14 has a rectangular slot 17 formed in a distal portion thereof for receiving a portion of the blade actuators 12A, 12B. The shaft 14 can further include at least one hole or bore formed therein for receiving a mating element configured to attach the shaft to an inner shaft 28 of the body. FIG. 5 illustrates first and second pins 19p, 19d that extend through the shaft 14 and couple to the inner shaft 28.

Figure 6A:
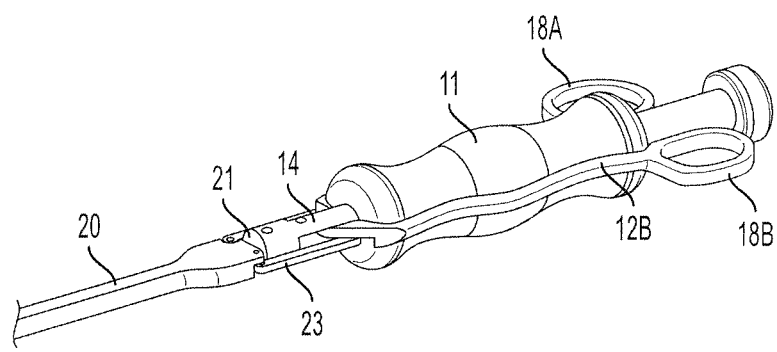
FIG. 6A is a perspective view of the handle assembly of FIG. 1 in a first, resting configuration.
Figure 6B:
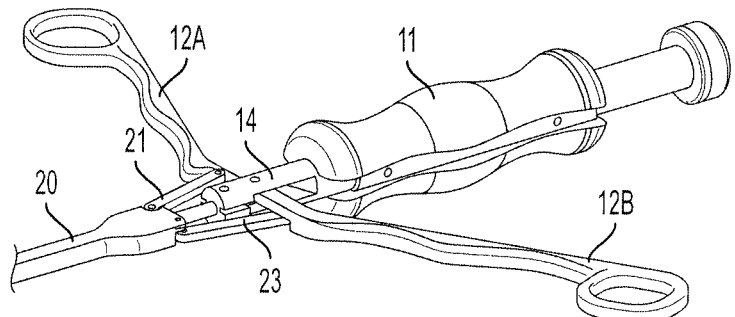
FIG. 6B is a perspective view of the handle assembly of FIG. 1 in a second, actuated configuration.

The handle assembly can further include first and second blade actuators, as shown in FIGS. 6A and 6B. In general, the first and second blade actuators 12A, 12B can be pivoted toward and away from the grasping handle 11 to move the respective blades relative to the distal housing 30. In the illustrated embodiment, the first and second blade actuators 12A, 12B have a generally elongate shape and proximal ends that terminate in a ring shaped finger hole 18A, 18B. Distal ends (not shown) of the first and second blade actuators 12A, 12B are positioned in a slot formed in a sidewall of the shaft 14 and can be pivotally coupled together via a pin (not shown). The blade actuators 12A, 12B can also be configured to fit inside the longitudinal recesses 13A, 13B formed along an outer sidewall of the central grasping handle 11. When the blade actuators 12A, 12B are positioned inside of the recesses and adjacent to the central grasping handle 11, as in FIG. 6A, the instrument is in a resting configuration with the blades in the distal housing being undeployed. When the blade actuators 12A, 12B are pivoted away from the recesses at a distance from the central grasping handle 11, as in FIG. 5B, the instrument is in an actuated configuration. In both the resting and actuated configurations, the first and second blade actuators 12A, 12B are offset and are no aligned in the same horizontal plane.

The first and second blade actuators can be connected to the shaft body in various ways, such as via first and second linkage bars shown in FIGS. 6A and 6B. In general, each linkage bar 21, 23 can have a proximal end and a distal end, and can have a generally rectangular elongate shape. In the illustrated embodiment, proximal and distal ends 21p, 21d, and 23p, 23d of the linkage bars 21, 23 have a circular shape with at least one bore formed therethrough for receiving a mating element, such as a pin. The distal end 21d, 23d of each of the first and second linkage bars 21, 23 can be pivotally coupled to the proximal end of the shaft body 20, and a proximal end of each of the first and second linkage bars can be pivotally coupled to the first and second blade actuators at a first pivot point and a second pivot point, respectively. The first and second blade actuators can be connected to the shaft body in other ways, such as using spot-welds.

Figure 7A:
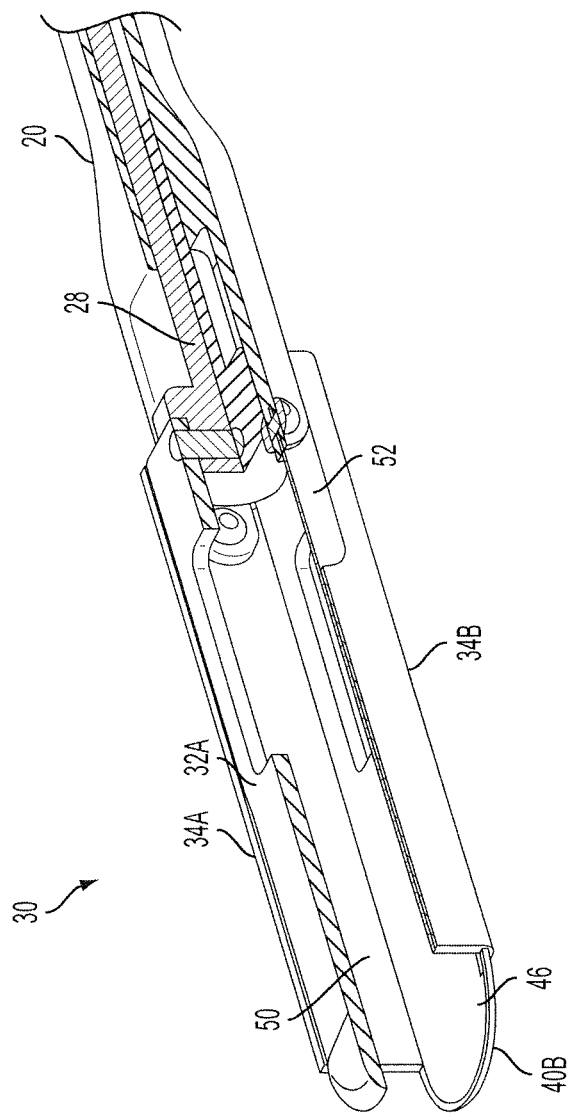
FIG. 7A is a perspective, semi-transparent view of the distal housing of FIG. 1 with first and second blades in a first, undeployed configuration.
Figure 7B:
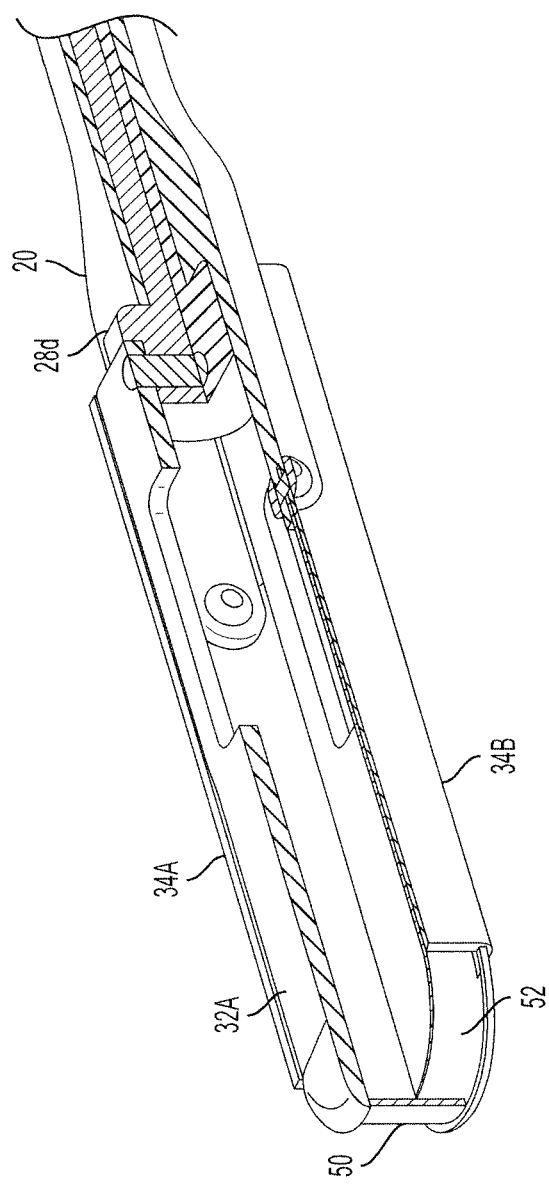
FIG. 7B is a perspective, semi-transparent view of the distal housing of FIG. 1 with first and second blades being in a second, deployed configuration.

FIGS. 7A and 7B show the plurality of blades disposed in the distal housing. As previously mentioned, first and second knife blades 50, 52 are configured to slide within and relative to the distal housing 30. The first and second knife blades 50, 52 can each have a proximal end 50p, 52p configured to mate with a respective arm 22A, 22B of the shaft body 20 and a distal end 50d, 52d configured to cut through a spinal disc. In the illustrated embodiment, the distal ends 50d, 52d of the first and second knife blades 50, 52 have complementary serrations. FIG. 6A shows the first and second blades in the undeployed configuration, the distal ends 50d, 52d being proximal to the distal edges 40A, 40B of the top and bottom walls 32A, 32B. In use, the first and second blades 50, 52 can be moved distally through the first and second tracks (one track being shown) until the distal ends of the first and second blades meet and interlock at the distal edge, at a point that is along the longitudinal axis of the distal housing 30, as in FIG. 6B.

Figure 8:
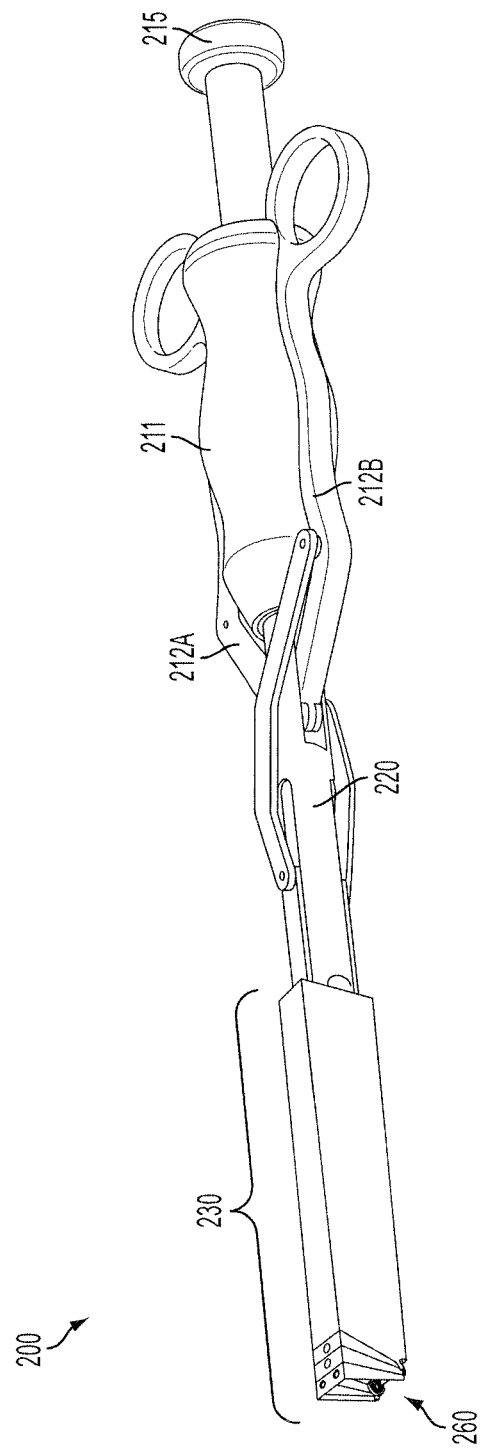
FIG. 8 is a perspective view of a second embodiment of a discectomy instrument.

FIG. 8 is a perspective view of another embodiment of a discectomy instrument. Similar to the previous embodiment, a discectomy instrument 200 includes a handle assembly 210, a shaft body 214, and a distal housing 230 configured to cut through a spinal disc. The handle assembly 210 includes first and second blade actuators 212A, 212B that are movable toward and away from a central handle 211 to move cutting blades. The shaft body 214 can be coupled to the handle assembly 210 and to the distal housing 230, and can have a generally elongate shape. The distal housing 230 can have an elongate rectangular shape and can include a swing blade assembly 260 that is movable relative to the housing 230. As will be discussed, the discectomy instrument 200 can be used to remove a disc when the spine is accessed via a lateral approach to the spine.

Figure 9:
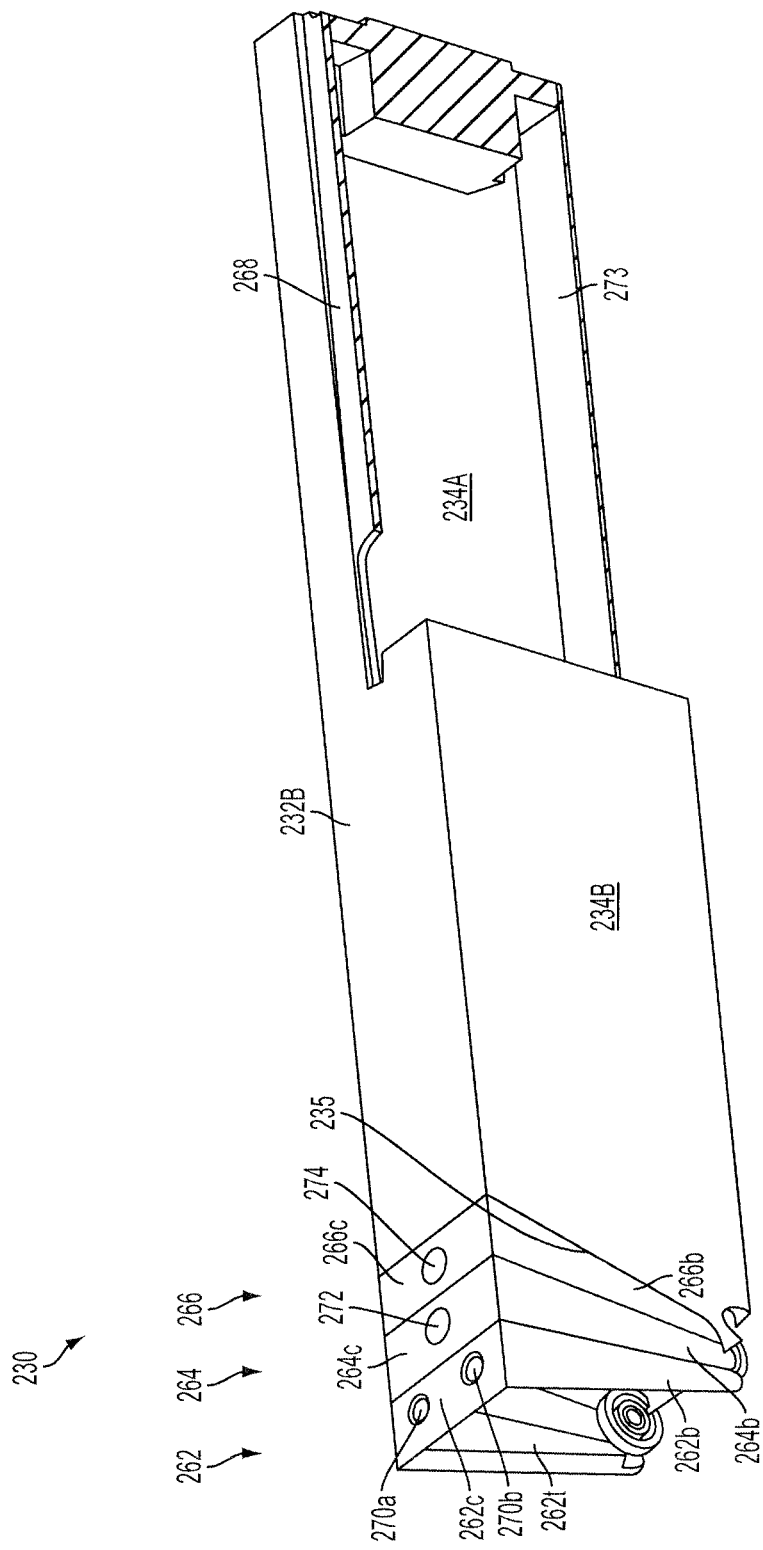
FIG. 9 is a perspective, partial cut away view of a distal housing of FIG. 8 that includes a swing blade assembly.

The distal housing can have various sizes, shapes, and configurations, and can have similar features as the distal housing 30 of the previous embodiment. As shown in FIG. 9, the distal housing 230 can resemble a box chisel and can have four walls, referred to herein as top and bottom walls 232A, 232B, and first and second lateral walls 234A, 234B that form an elongate, generally rectangular shape. In use, the top wall 232A can be configured to contact a first vertebral endplate and the bottom wall 234B can be configured to contact a second vertebral endplate. The first and second lateral walls 234A, 234B of the distal housing 230 can include an elongate slot 236 formed therein that can be used to extract a cut portion of a disc. The configuration of the walls can vary in a proximal-to-distal direction. For example, a proximal edge (not shown) of each of the top, bottom, and lateral walls 234A, 234B, 232B can be perpendicular to a longitudinal axis of the distal housing 230, while a distal edge of the lateral walls 232A, 232B can also be perpendicular to the longitudinal axis of the housing 230. Distal edges of the top and bottom walls can be tapered or angled in the proximal-to-distal direction to receive a swing blade assembly 260. FIG. 9 illustrates an angled distal edge 235 of the bottom wall 234B.

A swing blade assembly can be positioned at the distal most end of the discectomy instrument and can be used to cut a spinal disc. A swing blade assembly 260 can include a swing blade and one or more swing blade stabilizers that give strength to the swing blade and help confine the swing blade to an arc-shaped cutting path, as will be described. In the embodiment of FIG. 9, the swing blade assembly 260 has a lead swing blade 262, and first and second swing blade stabilizers 264, 266. In general, the lead swing blade 262 and the first and second swing blade stabilizers 264, 266 have substantially the same shape with different hinges so that they can pivot in the same plane.

The lead swing blade 262 can have various sizes, shapes, and configurations. In general, the lead swing blade 262 can have opposed top and bottom legs with a connecting element extending therebetween. The shape of the lead swing blade 262 is defined by three walls (top, bottom, and first lateral wall) of the distal housing 230. For example, top and bottom legs 262t, 262b of the swing blade can have a tapered, generally triangular shape and can be opposed to one another. An outer face of the top and bottom legs 262t, 262b can be configured to contact a vertebral endplate. The connecting element 262c can be substantially perpendicular to and can intersect with the top and bottom legs 262t, 262b, and the connecting element 262c can have a rectangular shape. A distal edge of the top and bottom legs 262t, 262b and a distal edge of the connecting element 262c can be sharpened and/or serrated for cutting through a disc. Each of the top and bottom legs 262t, 262b can terminate in a rounded portion or hinge having a first diameter. The lead swing blade 262 can be directly connected to a timing band 268 that is configured to advance the lead swing blade 262, such as using one or more rivets. The illustrated embodiment shows two rivets 270a, 270b extending through and being perpendicular to the connecting element 262c to couple the swing blade 262 to the timing band 268. Any number of mating elements can be used to attach the lead swing blade 262 to a timing band 268, and these elements can be positioned at various locations on the connecting element 262c.

As previously mentioned, swing blade stabilizers can provide stability to the lead swing blade. In the illustrated embodiment, first and second swing blade stabilizers 264, 266 are shown and have an identical shape as the lead swing blade 262. The first swing blade stabilizer 264 is positioned proximal to the lead swing blade 262 and is disposed in-between the lead swing blade 262 and second swing blade stabilizer 264. As shown, the first swing blade stabilizer 264 can have top and bottom legs 262t, 264b and a connecting element 264c. Top and bottom legs 262t, 264b can have a tapered, triangular shape that terminates in rounded portion or hinge having a second diameter. The second diameter can be smaller than the first diameter of the lead swing blade 262 so that the hinges of the first swing blade stabilizer 264 can be positioned within the hinges of the lead swing blade 262. The first swing blade stabilizer 264 can include one or more mating features that can couple to the timing band 268, as will be discussed. As shown, a rounded pin 272 can extend through an outer surface of the connecting element 264c toward an inner portion of the distal housing 230, in a direction that is perpendicular to the connecting element 264c. In the illustrated embodiment, the rounded pin extends through a center of the connecting element 264c, but a person skilled in the art will appreciate that the rounded pin can extend through the connecting element at various locations.

The second swing blade stabilizer 266 can have many of the features described with respect to the first swing blade stabilizer 264. In particular, the second swing blade stabilizer 266 can have an identical shape as the first swing blade stabilizer 264, including top and bottom legs 266t, 266b and a connecting element 266c. The top and bottom legs 266t, 266b can have a tapered, triangular shape that terminates in a rounded portion or hinge having a third diameter. The third diameter can be smaller than both the first and second diameters such that the hinges of the second swing blade stabilizer 266 can be positioned within the hinges of the lead swing blade 262 and the first swing blade stabilizer 264. As in the first swing blade stabilizer 264, the second swing blade stabilizer 266 can include one or more mating features that can couple to the timing band 268. As in the first swing blade stabilizer 264, a rounded pin 274 can extend through an outer surface of the connecting element 266c toward an inner portion of the distal housing 230, in a direction that is perpendicular to the connecting element 266c. The rounded pin 272 has a smaller diameter than the pin 272 in the second swing blade stabilizer 264, which can allow it to mate with a particular section of the timing band 268, as will be discussed. In the illustrated embodiment, the rounded pin 274 extends through a center of the connecting element 266c, but a person skilled in the art will appreciate that the rounded pin can extend through the connecting element 266c at various locations.

The discectomy instrument can also have a knife gate blade that can advance through a spinal disc and contact the lead swing blade to form a complete cut. While a knife gate blade 273 can have various configurations, in the illustration embodiment the blade 273 has a proximal end (not shown) coupled to a knife gate carriage that is in turn coupled to a knife gate actuator. In use, the knife gate blade 273 can slide along the lateral wall 232A (not shown in FIG. 9) of the distal housing 230. In some embodiments, the knife gate blade 273 can slide along a guide feature (not shown), such as a track formed on the lateral wall 232A. A distal end (not shown) of the knife gate blade 273 can be a sharpened and/or serrated cutting edge for cutting through a spinal disc. The knife gate blade 273 can also entrap cut disc material and force the material into the distal housing 230 for removal from the disc space. While the knife gate blade 273 can be formed from various materials, it is preferably made from a shape memory material such as nickel titanium (Nitinol).

The blade actuators can be operatively coupled to the knife gate blade and the swing blade assembly in various ways. In some embodiments, a timing band 268 can operatively couple the swing blade actuator 212B to the swing blade assembly 260. The timing band 268 can have an elongate, rectangular shape with a small thickness and the timing band 268 can have proximal and distal ends 268p, 268d, and first and second opposed, lateral faces. The proximal end 268p of the timing band 268 can be coupled to a distal end of a swing blade linkage (not shown), while the distal end 268d of the timing band 268 can be coupled to the lead swing blade 262. In this embodiment, the timing band 268 and the first swing blade 262 are coupled via two rivets 270a, 270b, and thus the timing band 268 has two holes 276a, 276b formed in the distal end 268d that can receive the rivets 270a, 270b. In use, a first lateral face of the timing band 268 can slide against an inner surface of the lead swing blade 262 and an inner surface of each stabilizer 264, 266.

The timing band can have various features that facilitate pivotal movement of the swing blade assembly via first and second hinges. In one embodiment, the timing band 268 can have a plurality of slots formed along a longitudinal axis thereof that can interact with features on the swing blade stabilizers. A first slot 280 can have a proximal portion 280p and a distal portion 280d, as shown in FIG. 10A. In the illustrated embodiment, the proximal portion 280p of the slot has a width and the distal portion 280d of the first slot 280 has a width that is greater than the width of the proximal portion 280p. These widths correspond to a diameter of the pin 272, 274 that extends through each swing blade stabilizer. More specifically, a width of the proximal portion 280p can be substantial equally to a diameter of the pin 272 extending through the first swing blade stabilizer 264, and a width of the distal portion 280d can be greater than a diameter of the pin 272. A second slot 278 can be positioned proximal to the first slot 280, and a width of the second slot 278 can be substantially equal to a diameter of the pin 274 extending through the second swing blade stabilizer 266. A longitudinal length of the slot 278 and a longitudinal length of portions 280p, 280d of the slot 280 can determine when the swing blade stabilizers are advanced, and this in turn depends on a position of the lead swing blade 262 along the arc-shaped. As shown in FIG. 10B, when the swing blade assembly 260 is in the fully deployed configuration, the lead swing blade 262 can be angulated at an angle θ greater than 135° about the hinge, relative to the first, undeployed configuration. For example, when the swing blade assembly 260 is in the fully deployed configuration, it can be positioned at an angle that is less than or equal to 165° degrees from an axis of approach of the instrument 200 into the disc. In the fully deployed configuration, the first and second stabilizers 264, 266 can be evenly spaced apart at angles of about 30°. In other embodiments, the swing blade assembly can have a greater or lesser number of swing blade stabilizers that can be timed in various ways and that the stabilizers can spaced at different angles relative to one another. Accordingly, an angular spacing of the elements and the angle of the swing blade 262 in the fully deployed configuration can vary.

Figure 11A:
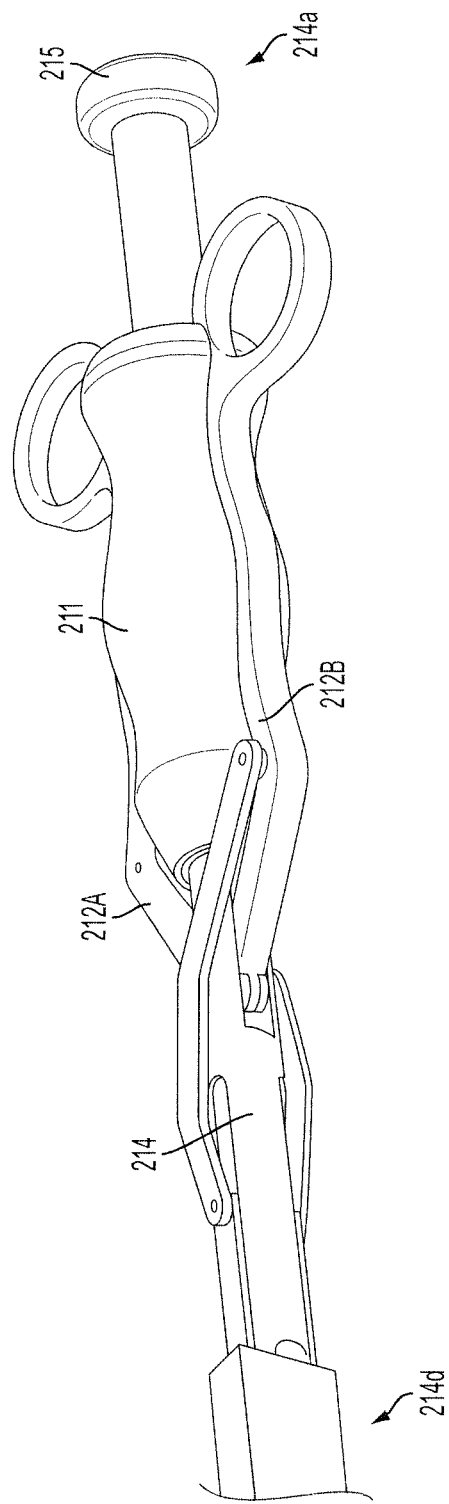
FIG. 11A is a perspective view of the instrument of FIG. 8 showing a handle assembly and shaft, the handle assembly being in a resting configuration.

The discectomy instrument 200 can have a shaft body 214 that forms a backbone of the device. As shown in FIG. 11A, the shaft 214 is an elongate, cylindrical body with proximal and distal ends 214p, 214d. The proximal end 214p of the shaft 214 can terminate in a striking head 215 having a cylindrical shape and a flattened, substantially planar proximal surface 215a. The distal end 214d of the shaft can be coupled to and reside within the box chisel using various techniques, such as press-fit, spot-weld, pins, etc. As shown in FIG. 11B, a mid-portion of the shaft 214 has a rectangular slot 282 formed therein for receiving a distal portion of the actuation handles 212A, 212B.

Figure 11C:
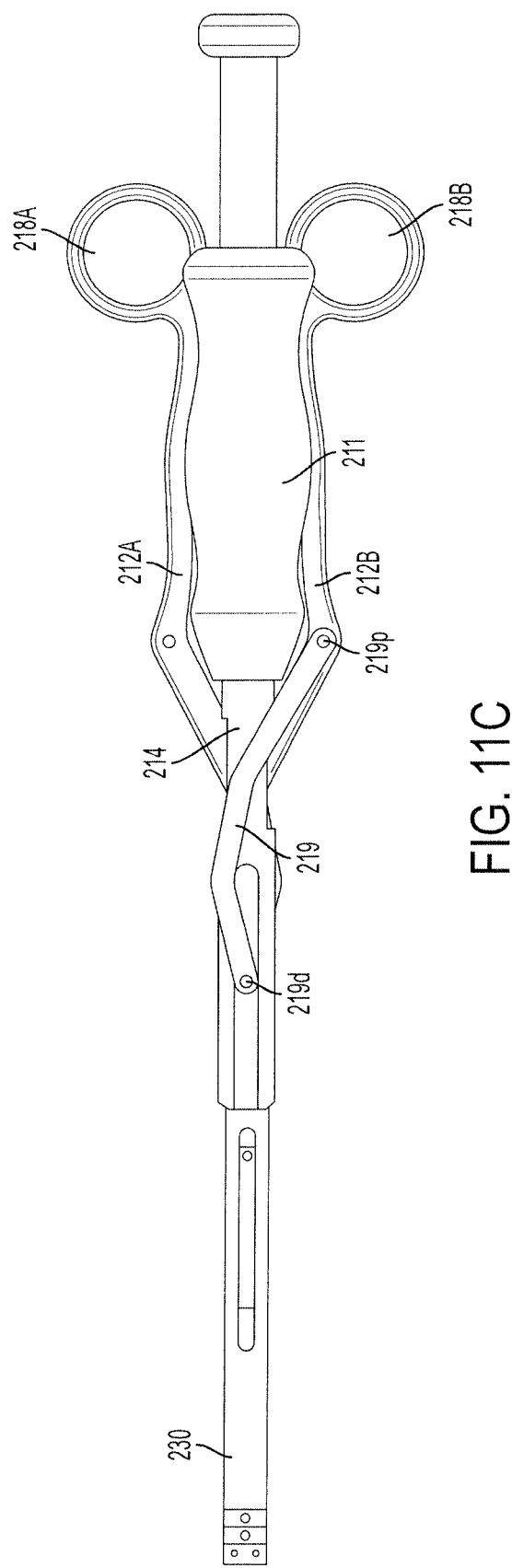
FIG. 11C is a side view of the instrument of FIG. 11B rotated 90°.

The handle assembly 210 of the discectomy instrument 200 can have similar features as the handle assembly of the previous embodiment. As shown in FIG. 11C, the handle assembly 210 can include a grasping handle 211. The grasping handle 211 can be disposed around and can be slidable relative to a shaft, and a hammer can be used to strike the proximal surface 215a of the head 215 of the shaft 214 to drive the instrument through a body. In another embodiment, the grasping handle 211 can be stationary relative to the shaft 214, and integrally formed with or molded to the shaft 214. As in the previous embodiment, the grasping handle 211 can further include one or more depressions or longitudinal recesses (not shown) configured to receive blade actuators 212A, 212B therein. First and second longitudinal recesses extend in a proximal to distal direction relative to a longitudinal axis of the grasping handle 211. These longitudinal recesses can also have one or more mating features (not shown) configured to hold the blade actuators 212A, 212B substantially flush against the grasping handle 211, as previously described.

The handle assembly can further include two blade actuators, as shown in FIGS. 11A-11C. The two blade actuators are referred to herein as a knife gate actuator 212B and a swing blade actuator 212A because pivotal movement of the actuators 212A, 212B toward and away from the grasping handle 211 moves the respective swing blade/knife gate blade relative to the distal housing 230. In the illustrated embodiment, the actuators 212A, 212B have a generally elongate shape and proximal ends that terminate in a ring hole 218A, 218B. Distal ends (not shown) of the actuators 212A, 212B are positioned in the rectangular slot 282 formed in a sidewall of the shaft 214 and can be pivotally coupled together via a pin. The actuators 212A, 212B can be configured to fit inside the longitudinal recesses formed along an outer sidewall of the handle 211. When the blade actuators 212A, 212B are positioned inside of the longitudinal recesses in the handle 211, the instrument is in a resting configuration with the blades in the distal housing 230 being undeployed. When the blade actuators 212A are pivoted away from the longitudinal recesses in the handle 211, the instrument is in an actuated or deployed configuration.

Two linkages can extend between and operatively couple the blade actuators to the blade in the distal housing. The linkages are referred to herein as swing blade linkage and knife gate blade linkage because movement of the linkage controls movement of the respective blade. As shown in FIG. 11C, swing blade linkage 219 can have an elongate shape with first and second bends, and proximal and distal ends 219p, 219d. The proximal end 219p of the swing blade linkage 219 can be coupled to the blade actuator 212B at a mid-portion of the swing blade actuator 212B. In certain aspects, the proximal and distal ends 219p, 219d can have at least one bore formed therethrough for receiving a mating element, such as a pin. A knife gate blade linkage (not shown) can have the same features as the swing blade linkage 219 and can function in the same way, i.e., couple to the knife gate blade actuator and the knife gate blade. In use, when the blade actuators 212A, 212B are pivoted away from the central handle 211, the linkages can move distally and exert a force on the respective blades to advance the blade distally and/or along the arc-shaped path to cut a spinal disc.

Various methods can be used to remove a spinal disc from a patient. While these methods are explained herein with respect to the discectomy instruments 100, 200 previously described, a person of ordinary skill in the art will be appreciate that other devices can be used to remove a spinal disc. In general, a discectomy procedure can begin by preparing a patient and locating a spinal disc using known techniques. In one embodiment, the disc space and a desired location for an incision can be identified using fluoroscopy. After the disc is located, the incision can be formed in the patient. As will be appreciated by a person skilled in the art, the location of the incision can depend on the particular approach used to access the spine, e.g., lateral, posterior, anterior, etc.

In one embodiment, a spinal disc can be removed from a patient using a lateral approach. The spinal disc can be located using lateral fluoroscopy and an incision can be formed in a side of the patient. In one embodiment, one or more dilators can be sequentially inserted into the incision and can be positioned flush with a vertebra. A position of the dilators can be monitored using fluoroscopy. A retractor can be inserted over the dilators and can be expanded to provide access to the disc space. In certain aspects, the retractor can have a plurality of blades that can be inserted in the disc space and expanded to distract the disc space. A height of the disc space can be confirmed using the retractor and/or by fluoroscopy. A height of the distal housing of the instrument can be selected to correspond to a height of the disc space. In one embodiment, the height of the distal housing can be substantially equal to the disc space. In another embodiment, the height of the distal housing can be greater than the disc space so that the instrument can distract the disc space when it is inserted therein.

Figure 12A:
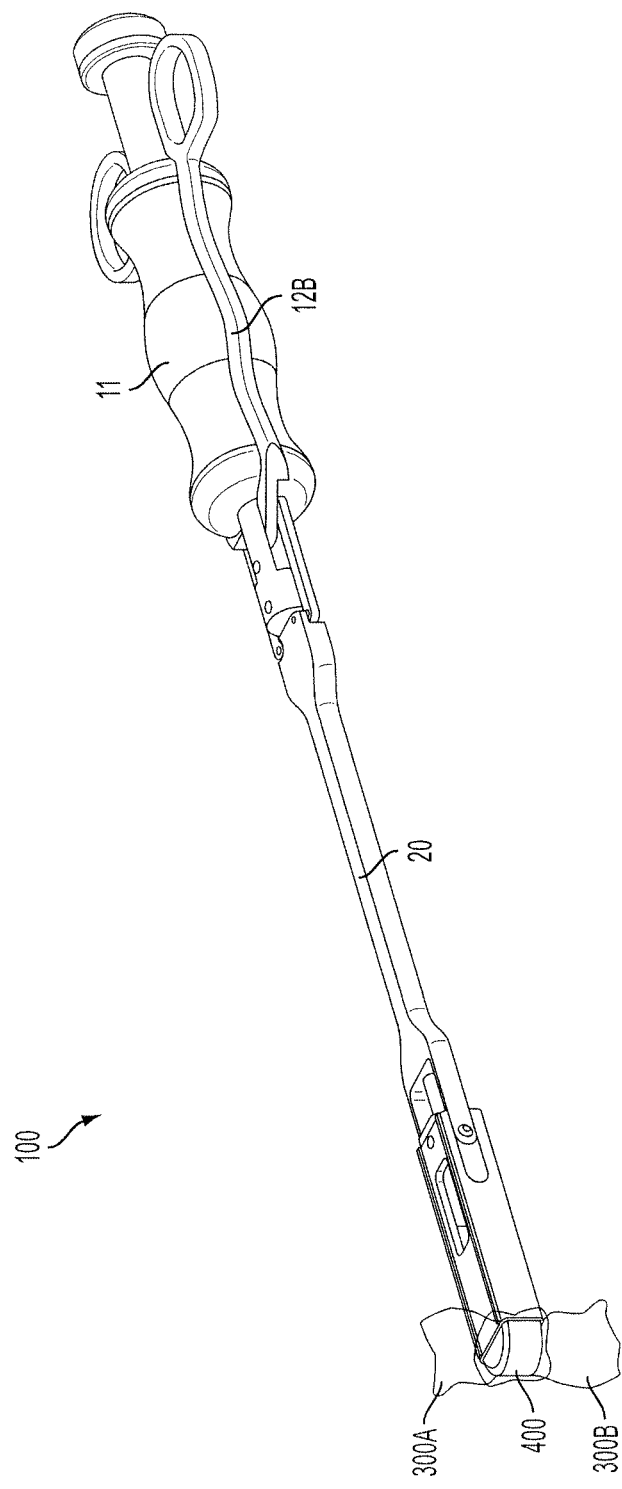
FIG. 12A is a perspective view of the instrument of FIG. 1 inserted between vertebrae in with the blades in the undeployed configuration and the handle assembly in the resting configuration.

After the disc space is accessed, a discectomy instrument can be inserted into the patient. In one embodiment shown in FIGS. 12A-12C, the discectomy instrument 100 can be inserted through the retractor in the undeployed configuration with first and second actuators 12A, 12B positioned in recesses of the grasping handle 11 in the resting configuration. The discectomy instrument 100 can be driven through tissue and toward a spinal disc 400 in various ways. For example, the sharpened distal portion 40A, 40B of the distal housing 30 can be manually advanced through tissue or can be advanced using an additional tool, such as a hammer. In one embodiment, a hammering force can be applied to the proximal head 15 of the handle assembly 10 to drive the instrument through tissue, such as a spinal disc. Preferably, the distal edges 40A, 40B of the top and bottom sides 32A, 32B are advanced through the disc 400 until the distal edges 40A, 40B are positioned adjacent to a lateral wall of the disc 400 so that the instrument 100 can remove a substantial portion of the disc. A person of ordinary skill in the art will appreciate that the distal portion of the top and bottom sides can be positioned at various locations within the disc. Optionally, a height of the distal housing 30 can distract or push apart endplates of vertebra 300A, 300B to increase a size of the disc space and decompress the vertebrae 300A, 300B.

Figure 12B:
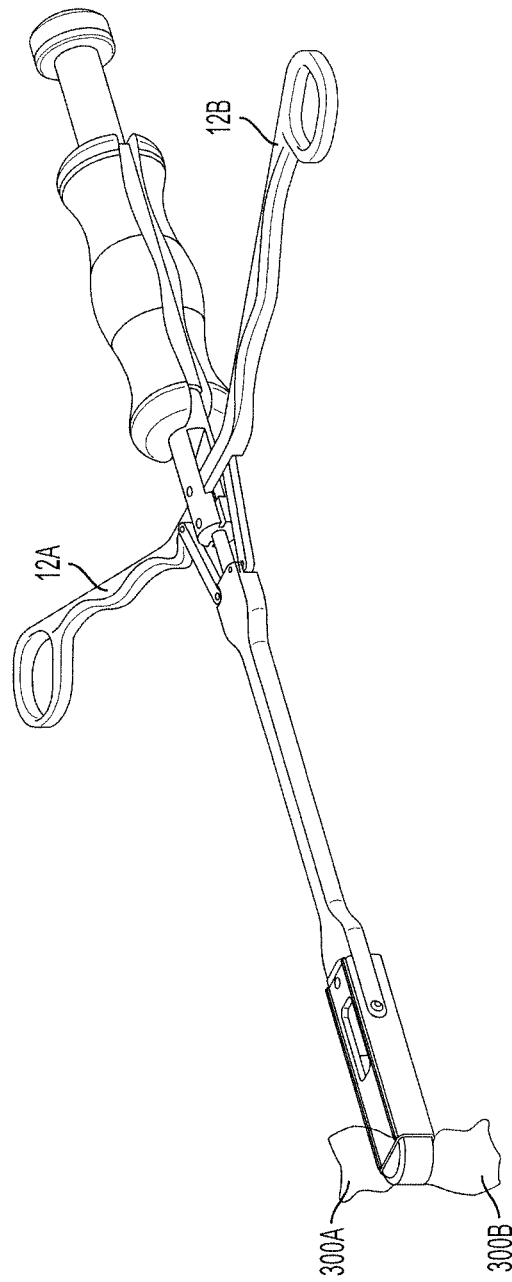
FIG. 12B is a perspective view of the instrument of FIG. 1 in a deployed configuration, cutting through a spinal disc.
Figure 12C:
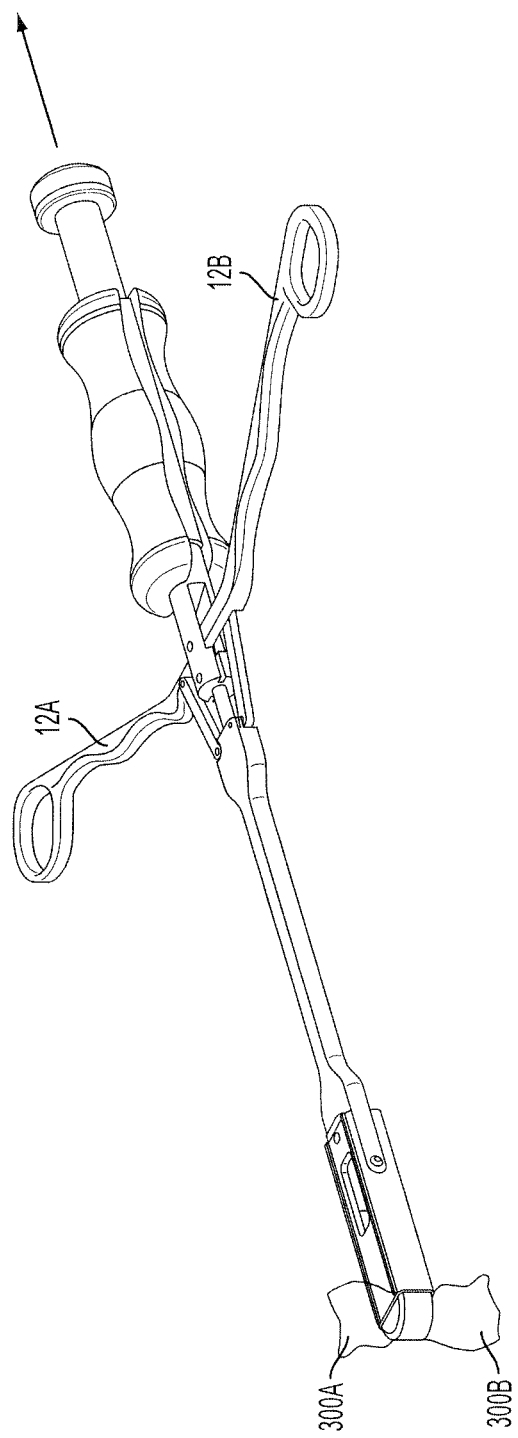
FIG. 12C is a perspective view of the instrument of FIG. 1 being removed from a patient.

When the distal housing 30 of the device 100 is in a desired position relative to the spinal disc 400, the cutting blades 50, 52 can be deployed from the distal housing 30. In one embodiment, a user can grasp the finger holes 18A, 18B of the first and second actuators 12A, 12B and simultaneously pivot the first and second actuators 12A, 12B outwardly, away from the central grasping handle 11. Pivotable movement of the actuators 12A, 12B can cause first and second links 21, 23 to exert a force on the shaft body 20 to move the shaft body 20 distally relative to the inner shaft 28. Additionally, the first and second arms 22A, 22B of the shaft body 20 can move distally within the recesses 42A, 42B formed in the distal housing 30. And because each arm 22A, 22B is coupled to a knife blade 50, 52, the knife blade 50, 52 can move within the guide feature 44, 46 formed in the distal housing 30 and cut through a spinal disc. In certain aspects, progression of the knife blades 50, 52 through the disc can be monitored using tactile feedback. In one embodiment, the pivoting force can be applied to the actuators 12A, 12B until the two knife gate blades 50, 52 contact one another and until it is not possible to pivot the actuators 12A, 12B further, as shown in FIG. 12B. When the instrument 100 is in a fully deployed configuration with the actuators 12A, 12B pivoted at a maximum distance away from the central grasping handle 11, distal ends of the first and second knife gate blades 50, 52 can interlock and can be positioned along the longitudinal axis of the instrument 100. This can form a complete cut in the spinal disc 400, and the cut portion of disc 400 can thus be captured and positioned within the distal housing.

After the spinal disc 400 is cut, the discectomy instrument 100 and the cut portion of disc 400 can be removed from the patient. A proximal force, shown in FIG. 12C using an arrow, can be exerted on the handle assembly 10, manually or using an additional tool, to remove the instrument 100 and the disc 400. In one embodiment, the central grasping handle 11 can be slidable proximally until it contacts the proximal head 15 of the shaft 14. When the grasping handle 11 contacts the head 15, this can exert a proximal force on the instrument 100 to withdraw the instrument 100 from a patient. In certain aspects, after the instrument 100 is withdrawn from the patient, an extractor tool can be inserted in the elongate rectangular slot 36 formed in the distal housing 30 and can be used to remove the cut portion of the disc 400. The disc space can then be prepared to receive a spinal fusion cage, such as by injecting irrigation fluid into the disc space. The spinal fusion cage can have a height that can substantially correspond to a height of the cut portion of the disc. Additionally or alternatively, a leading end of the spinal fusion cage can substantially correspond to/match a shape of the far wall of the cut portion.

In another embodiment, the spinal disc can be removed from a patient using an anterior or posterior approach. This can be accomplished using discectomy instrument 200, shown inserted between vertebrae 400, 500 in FIGS. 13A and 13B. The method steps can be identical to or different from those described with respect to the discectomy instrument 100, and can be performed in the same or different order. As in the previous embodiment, the patient can be prepared using the techniques previously described. For example, the disc can be located and an incision can be made in a patient at the desired location. The disc space can be accessed using any of the techniques previously described, or using other techniques known in the art. Fluoroscopy can be used to visually monitor the procedure. As in the previous embodiment, a height of the distal housing of the instrument can be selected to correspond to a height of the disc space. For example, the height of the distal housing can be substantially equal to the disc space or the height of the distal housing can be greater than the disc space so that the instrument can distract the disc space when it is inserted therein.

Figure 13A:
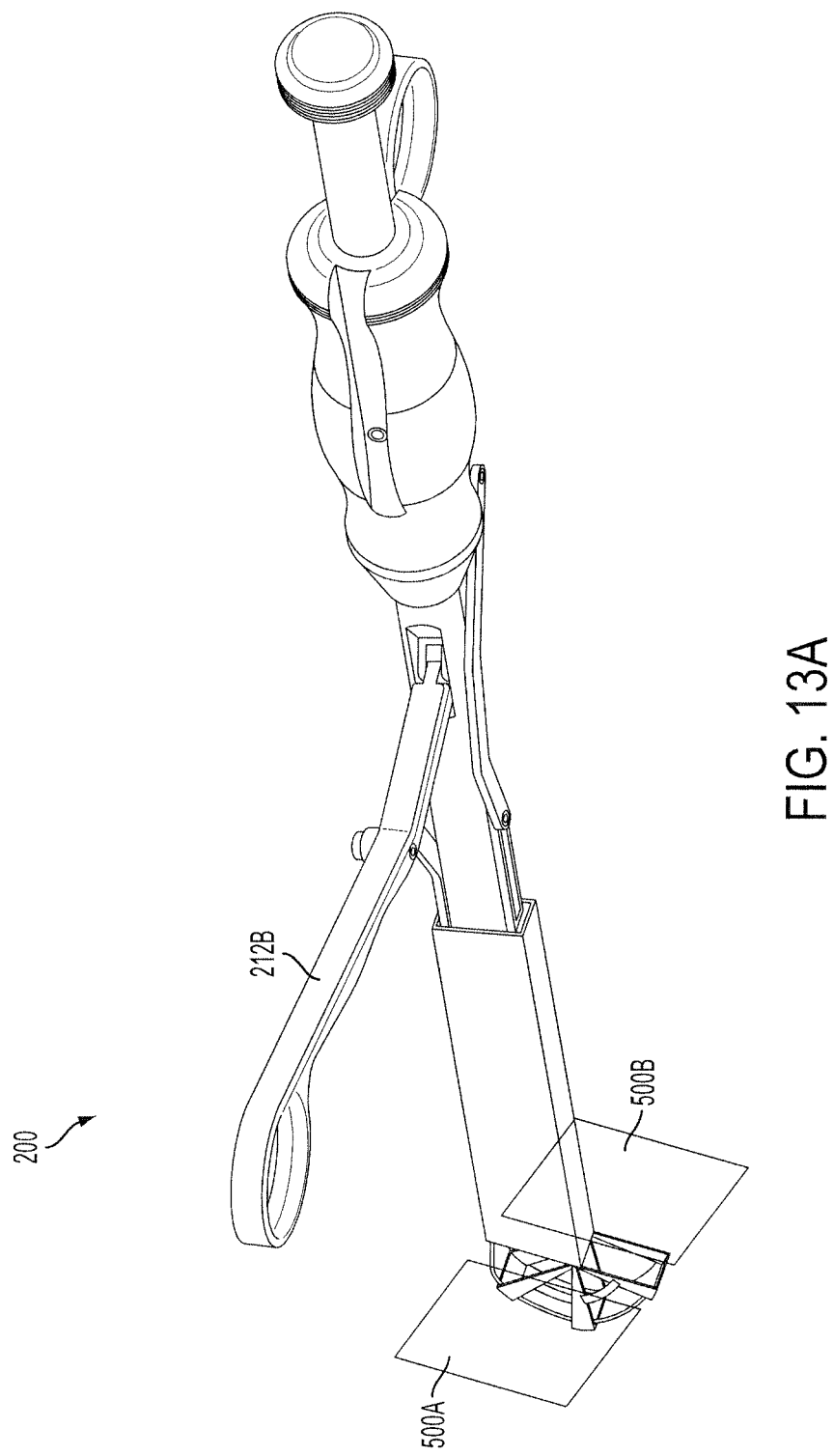
FIG. 13A is a perspective, cut-away view of the instrument of FIG. 9 with the swing blade assembly deployed into a spinal disc.

After the disc space is accessed, the discectomy instrument 200 can be inserted into the patient. In one embodiment, the discectomy instrument 200 can be inserted through the retractor in the undeployed configuration with first and second actuators positioned in recesses of the grasping handle 211, as shown in FIG. 13A. The discectomy instrument 200 can be driven through tissue and toward the spinal disc 400 in various ways, as previously described. Preferably, when the instrument 200 is positioned in the disc 400 immediately prior to the lead swing blade 262 being deployed, a distal edge of the connecting element 262c of the lead swing blade 262 is positioned along an outer lateral wall of the spinal disc 400 so that the instrument 200 can cut through a complete portion of the disc 400.

Figure 13B:
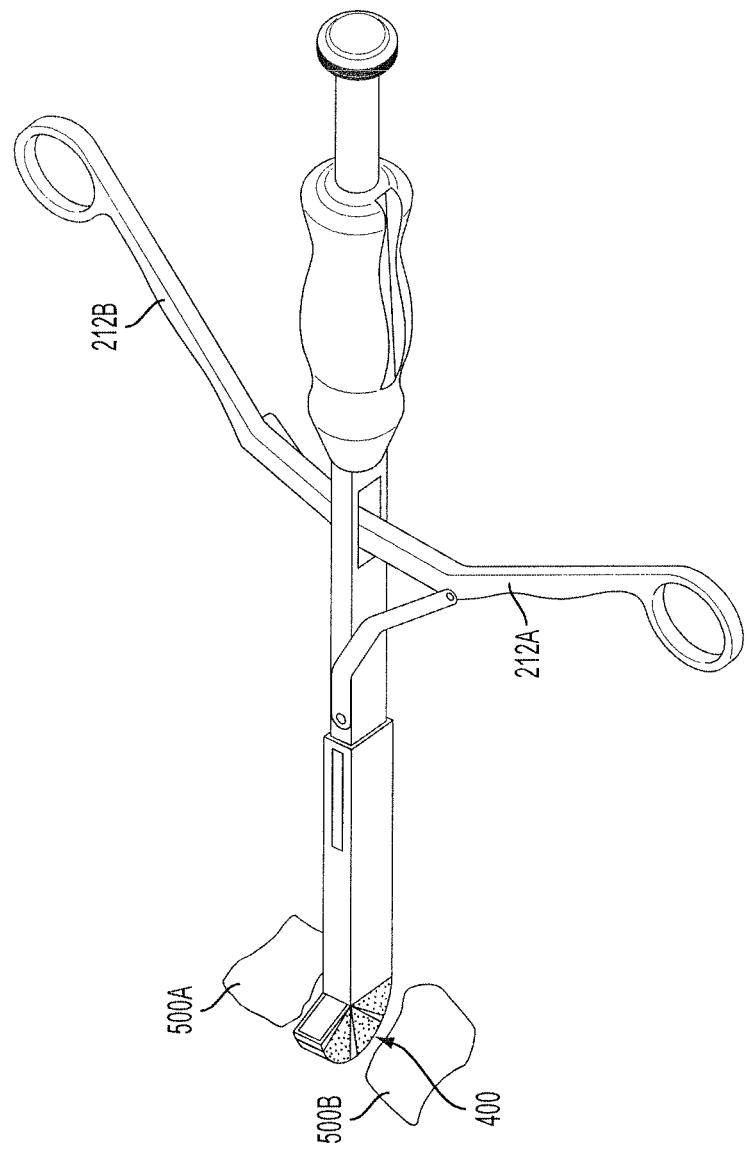
FIG. 13B is a perspective view of the instrument of FIG. 9 with a gate blade deployed and forming a complete cut through the spinal disc.

When the distal housing 230 of the device 200 is in a desired position relative to the spinal disc 400, the lead swing blade 262 can be deployed and moved away from the distal housing 230. As shown in FIG. 13B, the swing blade actuator 212B can be moved out of a recess and pivoted away from the grasping handle 211. Because the swing blade linkage 219 is coupled to the swing blade actuator 212B, pivotable movement of the swing blade actuator 212B can cause the swing blade linkage 219 to move distally, thereby moving the timing band 268 within the distal housing. Because the timing band 268 is coupled to the swing blade, as the timing band 268 moves distally, it exerts a distal force on the swing blade 262 that causes the swing blade 262 to move along the arc-shaped path. The arc-shaped path is determined in part by the position of the first and second hinges and the shape and dimensions of the lead swing blade 262.

As the pivoting force is applied and the swing blade actuator 212B is pivoted further away from the grasping handle 211, one or more swing blade stabilizers can move along the arc-shaped path of the swing blade 262. In illustrated embodiment, the instrument includes first and second swing blade stabilizers 264, 266. Continued advancement of the timing band 268 can cause the first pin 272 of the first swing blade stabilizer 264 to mate with and be received in the distal portion 280d and then the proximal portion 280p of the timing band 268. As the timing band 268 moves distally relative to the housing, the second pin 274 of the second swing blade stabilizer 266 can mate with and be received in the second slot 278 of timing band 268. The second swing blade stabilizer 266 can move along the arc-shaped path of the lead swing blade 262 and the first swing blade stabilizer 264. Progress of the lead swing blade 262 and/or the swing blade stabilizers 264, 266 can be monitored via tactile feedback. Movement of the lead swing blade 262 and/or the swing blade stabilizers 264, 266 can be stopped at any time, or can be reversed by pivoting the swing blade actuator 212B toward the central handle 211. When the instrument 200 is in a fully deployed configuration with the actuator 212B pivoted at a maximum distance away from the central grasping handle 211, the lead swing blade 262 can be pivoted at an angle of about 165 degrees relative to a longitudinal axis of the device 200.

After the swing blade actuator 212B is pivoted away from the central grasping handle 211 and the lead swing blade 262 is pivoted at a desired angle, the knife gate blade 273 can be advanced out of the distal housing 230. In one embodiment, the knife blade actuator 212A can be pivoted away from the central handle 211, and a knife blade linkage (not shown) can move distally and also move the knife gate blade 273 distally. This can move the knife gate blade 273 distally away from lateral wall 232 of the distal housing 230 and through track (not shown) in the lead swing blade 262 until it reaches the lead swing blade 262 and forms a complete cut. The cut portion of the spinal disc 400 can thus reside within the lead swing blade 262, first and second swing blade stabilizers 264, 266, and the timing band 268. With at least a portion of the spinal disc 400 being cut, the discectomy instrument 200 and the cut portion of the disc 400 can be removed from the patient. As in the previous embodiment, a proximal force can be exerted on the handle, manually or using an additional tool, to withdraw the instrument and the cut disc. In certain aspects, the central grasping handle 211 can be slidable proximally or an external tool can be used to withdraw the instrument 200 and the cut portion of the disc 400. In certain aspects, after the instrument is withdrawn from the patient, an extractor tool can be inserted in the elongate rectangular slot formed in the distal housing 230 and can be used to remove the cut portion of the disc 400. The disc space between vertebrae 400, 500 can be prepared to receive a spinal fusion cage, such as by injecting irrigation fluid into the disc space. The spinal fusion cage can have a height that can substantially correspond to a height of the cut portion of the disc. Additionally or alternatively, a leading end of the spinal fusion cage can substantially correspond to/match a shape of the far wall of the cut portion.

The devices and methods used herein can be configured to remove a portion of a spinal disc or an entire, complete portion of a disc. The volume of spinal disc removed from a patient in a single pass (e.g. inserting and deploying the device a single time) can depend in part on the radius of curvature of the arc-shaped path relative to a radius of curvature of the disc, and can depend on an initial position of the cutting blades relative to a size and shape of the spinal disc. By way of non-limiting example, the devices and methods disclosed herein are effective to remove at least 25% of the spinal disc by volume, at least 50% of the spinal disc by volume, but preferably, approach 100% removal of the spinal disc by volume. The volume of spinal disc removed can thus be substantial enough for a surgeon to then insert a shaver into the disc space to remove any residual material from the endplates of the vertebrae and cut through cortical bone and into cancellous bone.

A person skilled in the art will appreciate that the instruments disclosed herein can be used in conventional minimally-invasive and open surgical instrumentation, and also have application in robotic-assisted surgery. By way of non-limiting example, the spinal fusions referred to herein can be a transforaminal lumbar interbody fusion (TLIF) in which the lumbar spine is approached through an incision in the back, a posterior lumbar interbody fusion (PLIF), a direct lateral lumbar interbody fusion (DLIF), or an extreme lateral lumbar interbody fusion (XLIF).

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. For example, in some embodiments the distal housing of a discectomy instrument can be removed from the shaft and replaced after a single use, such as via a releasably attachment between the distal housing and the shaft. In other embodiments, the blade assemblies (swing blade assembly and/or knife gate blades) can be removed and replaced after one or more uses so that the instrument has a sharpened blade for cutting through a disc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A device for removing a spinal disc, comprising:
   a housing having four walls that form a substantially rectangular shape with an open interior configured to receive a cut portion of the spinal disc, the housing having a first cutting blade and a second cutting blade;
   a handle assembly including a handle, a first blade actuator and a second blade actuator, the first and second blade actuators being operatively coupled to the first and second cutting blades;
   an outer shaft having a proximal end coupled to the handle assembly and a distal end slidably coupled to the housing; and
   an inner shaft disposed in the outer shaft, the inner shaft having a first end coupled to the handle and a second end coupled to the housing;
   wherein pivoting the first blade actuator relative to the handle moves the first cutting blade along a first arc-shaped path through the spinal disc, and pivoting the second blade actuator relative to the handle moves the second cutting blade along a second arc-shaped path such that the second cutting blade contacts the first cutting blade, thereby cutting the spinal disc.

2. The device of claim 1, wherein the arc-shaped paths of the first and second cutting blades substantially correspond to a shape of a lateral surface of the spinal disc.

3. The device of claim 1, wherein the housing has a height that is greater than or substantially equal to a height of the spinal disc.

4. The device of claim 1, wherein the first cutting blade and the second cutting blade are configured to move within one or more tracks formed in the housing.

5. The device of claim 4, wherein distal ends of the first and second cutting blades are configured to interlock.

6. The device of claim 1, wherein the first and second blade actuators can be manually pivoted toward and away from the handle.

7. The device of claim 1, wherein the handle includes a first recess configured to receive the first blade actuator and a second recess configured to receive the second blade actuator.

8. The device of claim 7, wherein each of the first and second recesses include one or more mating features configured to hold the first and second blade actuators therein.

9. A device for removing a spinal disc, comprising:
a distal housing including:
superior and inferior walls,
first and second lateral walls,
first and second cutting edges extending beyond distal ends of each of the superior and inferior walls, and
first and second cutting blades configured to move relative to the distal housing;
a handle assembly including a handle, a first blade actuator, and a second blade actuator, the first and second blade actuators advancing the first cutting blade along a first path and the second cutting blade along a second path;
a shaft body extending between the distal housing and the handle assembly; and
an inner shaft disposed within the shaft body, the inner shaft being fixedly coupled to the distal housing and to the handle;
wherein the first and second paths are proximal to the first and second cutting edges of the distal housing.

10. The device of claim 9, wherein the first and second cutting edges are curved.

11. The device of claim 9, wherein a distal end of the shaft body includes first and second arms.

12. The device of claim 11, wherein the first arm of the shaft body is configured to slide within a first recess formed in the first lateral wall of the distal housing, and the second arm is configured to slide within a second recess formed in the second lateral wall of the distal housing.

13. The device of claim 9, further comprising a first track formed on an inner surface of the superior wall and a second track formed on an inner surface of the inferior wall, the first and second tracks defining the first and second curved paths of the cutting blades.

14. A device for removing a spinal disc, comprising:
a distal housing including:
superior and inferior walls,
first and second lateral walls,
first and second arc-shaped cutting edges extending beyond distal ends of each of the superior and inferior walls, and
first and second cutting blades configured to move relative to the distal housing;
a handle assembly including a handle, a first blade actuator that advances the first cutting blade along a first curved path that follows a periphery of the first cutting edge, and a second blade actuator that advances the second cutting blade along a second curved path that follows a periphery of the second cutting edge; and
a shaft body extending between the distal housing and the handle assembly,
wherein the first and second cutting edges are configured to penetrate tissue prior to the first and second cutting blades being advanced along the first and second curved paths.

* * * * *